Figure 1:
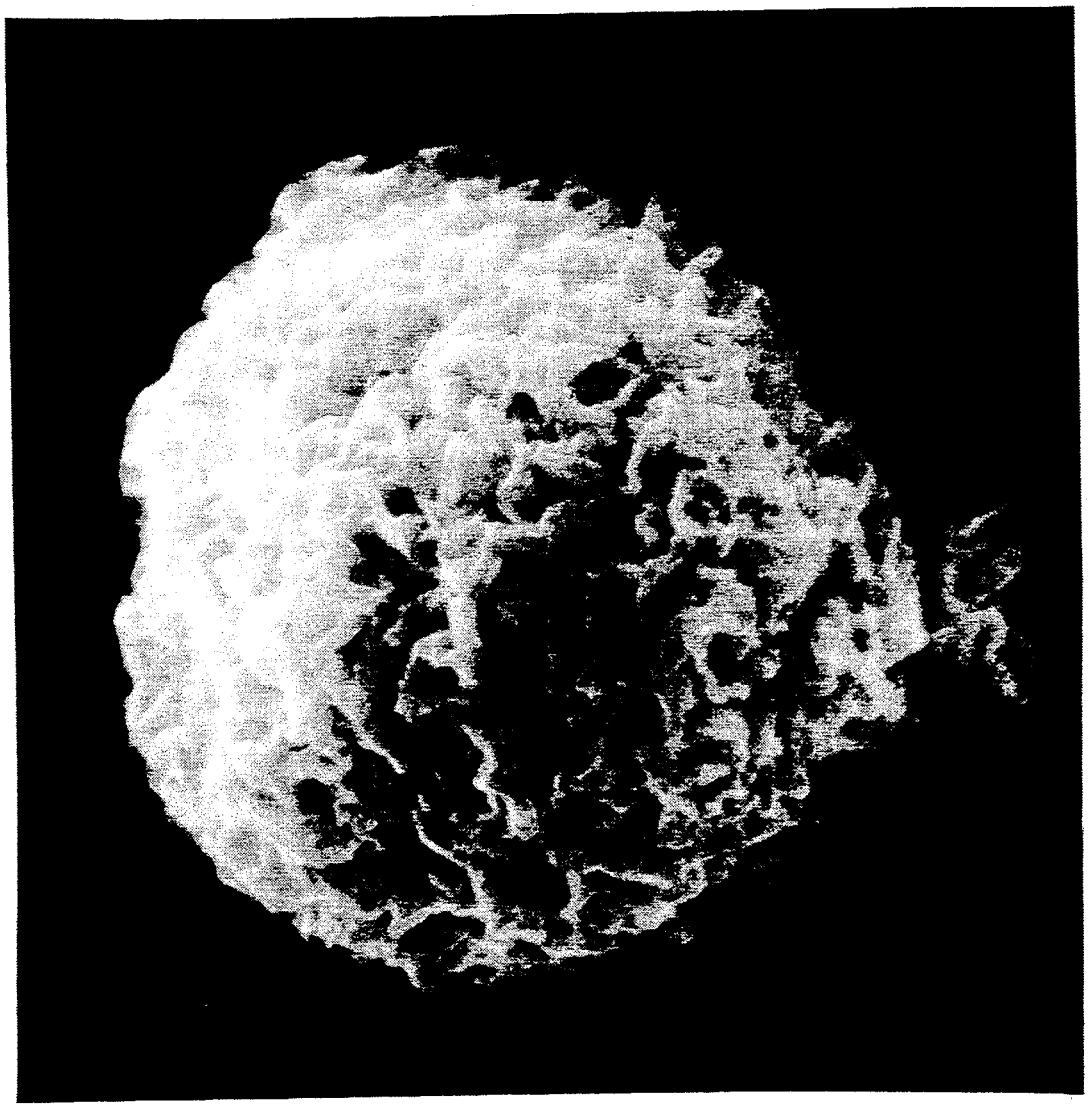

United States Patent [19]

Schutz et al.

[11] Patent Number: 5,153,156
[45] Date of Patent: Oct. 6, 1992

[54] PROCESS FOR MAKING EFFICIENT ANIONIC CLAY CATALYST, CATALYSTS MADE THEREBY, AND METHOD OF MAKING ISOPHORONE

[75] Inventors: Alain A. Schutz, Penn Township, Westmoreland County; Leonard A. Cullo, Hempfield Township, Westmoreland County, both of Pa.

[73] Assignee: Aristech Chemical Corporation, Pittsburgh, Pa.

[21] Appl. No.: 766,938

[22] Filed: Sep. 27, 1991

Related U.S. Application Data

[60] Continuation-in-part of Ser. No. 576,909, Sep. 4, 1990, Pat. No. 5,055,620, Division of Ser. No. 339,745, Apr. 18, 1989, Pat. No. 4,970,191.

[51] Int. Cl.⁵ .................. B01J 21/16; B01J 37/10
[52] U.S. Cl. ................................ 502/63; 502/80
[58] Field of Search ................ 502/63, 80, 412

[56] References Cited

U.S. PATENT DOCUMENTS

| | | | |
|---|---|---|---|
| 2,535,647 | 12/1950 | Millman et al. | 502/80 |
| 2,988,518 | 6/1961 | Milliken, Jr. | 502/80 |
| 3,337,633 | 8/1967 | Schmitt et al. | 260/586 |
| 3,539,306 | 11/1970 | Kumura et al. | 23/315 |
| 3,650,704 | 3/1972 | Kumura et al. | 23/315 |
| 3,879,523 | 4/1975 | Miyata et al. | 423/250 |
| 3,966,641 | 6/1976 | Csatar et al. | 502/80 |
| 3,981,918 | 9/1976 | Walton et al. | 260/586 C |
| 4,165,339 | 8/1979 | Reichle | 260/586 C |
| 4,351,814 | 9/1982 | Miyata et al. | 423/306 |
| 4,400,431 | 8/1983 | Henslee et al. | 428/402 |
| 4,458,026 | 7/1984 | Reichle | 502/80 |
| 4,476,324 | 10/1984 | Reichle | 568/388 |
| 4,535,187 | 8/1985 | Papa et al. | 568/353 |
| 4,539,195 | 9/1985 | Schanz et al. | 423/419 P |
| 4,656,156 | 4/1987 | Misra | 502/415 |
| 4,843,168 | 6/1989 | Drezdzon et al. | 558/357 |
| 4,962,237 | 10/1990 | Laycock | 568/618 |
| 4,970,191 | 11/1990 | Schutz | 502/341 |

*Primary Examiner*—Carl F. Dees
*Attorney, Agent, or Firm*—William L. Krayer

[57] ABSTRACT

Magnesium/aluminum synthetic anionic clay catalysts are made by spray-drying a slurry of a Mg/Al synthetic clay, making a plasticized mixture of the spray-dried clay with diatomaceous earth, forming, drying and calcining the formed dried mixture. The catalyst is useful for making isophorone by the condensation of acetone.

10 Claims, 1 Drawing Sheet

PROCESS FOR MAKING EFFICIENT ANIONIC CLAY CATALYST, CATALYSTS MADE THEREBY, AND METHOD OF MAKING ISOPHORONE

RELATED APPLICATION

This application is a continuation-in-part of co-pending U.S. patent application Ser. No. 576,909, filed Sept. 4, 1990, now U.S. Pat. No. 5,055,620 which is a division of U.S. patent application Ser. No. 339,745, filed Apr. 18, 1989 now U.S. Pat. No. 4,970,191.

TECHNICAL FIELD

This invention pertains to catalysts made from anionic clay materials, including a process of making catalyst pellets suitable to be used efficiently for diffusion sensitive reactions such as aldol condensation of acetone.

BACKGROUND ART

Anionic clay materials comprise synthetic or natural layered mixed hydroxides exhibiting anionic exchange abilities. The crystal structure of such compounds comprises positively charged hydroxide layers intercalated with anions and water molecules. This constitutes a very broad family of minerals since they can be formed with most divalent and trivalent cations as well as most inorganic and organic anions. Pyroaurite, hydrotalcite and sjogrenite can be taken as examples of natural minerals having this structure. See H. F. W. Taylor, Mineralogical Magazine, 39, 304, pp. 377-389, 1973. A general formula for the clay materials of interest here can be proposed as follows:

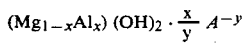

$$(Mg_{1-x}Al_x)(OH)_2 \cdot \frac{x}{y} A^{-y}$$

where x is a number less than 1, A is an anion, and y is the valence of the anion.

Natural deposits of such minerals can be found but are usually mixed with other minerals and impurities which prevent any commercial utilization. However, these anionic clays can be readily prepared synthetically by various methods and raw materials such as described in U.S. Pat. Nos. 3,539,306, 3,650,704, 3.879,523, 4,560,545, 4,539,195, 4,656,156, 4,351,814 and 4,458,026. Such synthetic materials are used in the pharmaceutical industry as antacids, in the chemical industry as halogen scavengers in polyolefins, as adsorbents, and as catalysts for chemical reactions such as isomerization of olefins (U.S. Pat. No. 4,657,307), aldol condensation (U.S. Pat. No. 4,476,324), and methanol synthesis (S. Gusi et al., Preparation of Catalysts IV, p. 753, Elsevier, 1987). Hydrogenation catalysts prepared by adsorbing ruthenium ions on a hydrotalcite support are disclosed in U.S. Pat. No. 4,923,837. A catalytic process for polymerizing epoxides using hydrotalcite catalysts is described in U.S. Pat. No. 4,962,237. Pillared hydrotalcites and catalysts using pillared hydrotalcites are described in U.S. Pat. Nos. 4,774,212 and 4,843,168, respectively.

Synthesis methods which use stochiometric amounts of raw materials without any excess of salts are preferred. Such a method is described in parent application, now U.S. Pat. No. 4,970,191 (which is incorporated herein by reference) and offers many manufacturing advantages relative to other methods, commonly known as co-precipitation methods. The main advantage of such a method is that the absence of salts obviates the washing/filtering step and produces a higher purity material. This also allows one to make gel-like materials which are usually impossible to filter but are preferred for making high crush strength catalyst pellets.

The potential for forming the material into strong pellets is imperative for the use of the material as catalysts in industrial reactors. In cases where pore diffusion affects the selectivity of the reaction, it is critical to use the smallest catalyst pellets which can be used without an unnecessarily large pressure drop. Moreover, such catalyst pellets should also contain large access pores to attain good diffusion. Both of these criteria can only be satisfied with a material and a forming method which have the ability of giving good mechanical properties.

U.S. Pat. Nos. 4,476,324 and 4,458,026 claim the calcination of the filter solids as catalysts (claim 1, steps 5-6). They also propose to form the calcined powders by extrusion or compression into tablets (page 3, lines 57-62).

U.S. Pat. No. 4,400,431 uses anionic clay materials to synthesize spinels and also proposes to form the fired material into shapes by compression and sintering. The final products can be used as catalyst carriers.

U.S. Pat. No. 4,656,156 describes the forming of calcined synthetic hydrotalcites with activated alumina to obtain composites with good mechanical strength and useful as adsorbents.

It is known in the art of forming catalysts that tableting powders produces strong pellets. However, such pellets are difficult and expensive to make in sizes less than ⅛ in diameter, which are desirable for diffusion sensitive reactions. The use of a binder such as aluminum oxyhydroxide is also not suitable because the resulting alumina, obtained after calcination, can catalyze non-desirable reactions.

The aldol condensation of acetone to isophorone is known to occur in the liquid phase in the presence of homogeneous bases such as sodium or potassium hydroxide. Several processes are described in U.S. Pat. Nos. 3,337,633, 3,981,918 and 4,059,632. Most of the isophorone product today is manufactured via these processes. Disadvantages of the liquid phase process are long residence time, high pressure equipment, high capital cost and waste streams containing the used catalyst.

Heterogeneous catalysts for aldol condensation of acetone to isophorone and mesityloxide are described in U.S. Pat. Nos. 3,946,079, 4,476,324, 4,535,187 and 4,970,191. U.S. Pat. No. 4,535,187 describes a calcium on alumina catalyst and states, (page 1, lines 48-51), "the co-precipitated mixed oxide catalysts have the drawback of exhibiting poor catalyst manufacturing reproducibility and are expensive". For this reason, the calcium on alumina catalyst is preferred. However, mesityloxide is the principal product and the crude isophorone is highly colored. A treatment of the crude isophorone is necessary to obtain low color refined isophorone and is described in U.S. Pat. No. 4,434,301.

Catalysts made with anionic clay materials have been tested with microreactors or pulse reactors as described in U.S. Pat. No. 4,476,324 for the aldol condensation of acetone. The catalyst is usually in the form of a fine powder and provides good selectivities (mesityl oxide and isophorone), i.e. 85 wt%. The mole ratio of mesityloxide to isophorone is also substantially lower than the one obtained with the calcium on alumina catalyst. However, when a commercially utilizable catalyst is used, in the form of ¼" tablets, the selectivity decreases to 77% at 23% conversion of acetone. Such selectivity is inadequate for making isophorone cheaply and for minimizing the co-production of heavy condensation products. The decrease of selectivity from about 85 to 77 wt% is caused by pore diffusion limitations.

It is, therefore, an object of this invention to provide an efficient aldol condensation catalyst for converting acetone to mesityloxide and isophorone.

It is also an object of this invention to provide an efficient catalyst which can be used in a commercial vapor phase reactor.

SUMMARY OF THE INVENTION

The present invention provides a process of manufacturing anionic clay based catalysts which satisfies the above objects. This invention is applicable to many anionic clay materials, whatever is the method of preparing or synthesizing such materials. It is specifically appropriate to anionic clay based catalysts used for catalyzing diffusion sensitive reactions such as consecutive reactions and more specifically aldol condensation of ketones or aldehydes.

Such objects are met by forming strong, small and macroporous anionic clay catalyst pellets by the process which comprises the steps (a), (b), (c) and (d):

(a) Spray-drying a water suspension of synthetic anionic clay into solid particles having sizes between about 10 and 100 microns in diameter and having a residual water content of about 5 to about 50%.

The synthetic anionic clay which we use in our invention have the formula

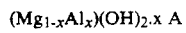
$(Mg_{1-x}Al_x)(OH)_2 \cdot x\ A$ where x is a number from 0.1 to 0.5, A is a univalent organic anion of the formula RCOO—, where R is $C_nH_{2n+1}$ and n is 0-4.

As is known in the art, spray-drying is a process wherein a slurry of material is atomized into a hot-environment. In our process, we use a pumpable slurry of about 2% to about 20% solids and atomize it to sizes about 1 micron to about 150 microns. The spray environment is maintained such that most of the water in the slurry is driven out so the free-falling particles have only about 5% to about 25% water when they come to rest. This process makes particles having randomly shaped open cells not unlike a honeycomb or open-called sponge, i.e. see U.S. Pat. No. 4,562,268.

A typical solid particle made by spray-drying a synthetic anionic clay of our invention is shown in FIG. 1 and is characterized by having unexpected and unique structure and properties which can be characterized by the properties of dispersibility and swelling capability. The spray-dried anionic clay materials, when mixed with water, form a homogeneous gel because the particles can be instantaneously rehydrated and dispersed into their original crystallites. For comparison, powder obtained by milling, room temperature dried and/or oven dried, and/or calcined anionic clay materials, without spray-drying, do not disperse readily. During the drying in an oven, one can observe that the homogeneous gel material shrinks so severely that it forms dense particles which are difficult to rehydrate and be redispersed into small particles or gel. To demonstrate that the structure of the spray-dried particles is the key property for dispersibility, a sample of spray-dried particles has been further dried in an oven at 200° C. We found that such material can be dispersed and rehydrated as well as the original spray-dried powder.

As a measurement of complete rehydration, a sample of the synthetic clay made by the method of U.S. Pat. No. 4,970,191 was spray-dried and dispersed in water.

The suspension is then dried at room temperature on a glass slide, to allow orientation, and an X-ray diffraction pattern is recorded. This method is commonly used in Clay Mineralogy and is described in Crystal Structures of Clay Minerals and their X-ray Identification (edited by G. W. Brindley and G. Brown, Mineralogical Society, London). It allows one to measure the d-spacing, i.e. the distance between the hydroxide layers, which is mainly related to the size of the anions, for dehydrated and non-swelling samples, and to the amount of water molecular layers for the samples exhibiting larger d-spacings. As shown in Example 1 infra, the d-spacing of the synthetic clay material, dried at room temperature, was about 12.2 Å A and collapses to about 8.7 Å A after drying at 110° C. After spray-drying at a temperature of about 100° C. and rehydration, the d-spacing returns to 12 AÅ.

In order to have large access pores for the reactant and the products of the reaction, inert macroporous material can be added and mixed with the anionic clay before or after it is spray-dried. The desired properties of the macroporous material are: high pore volume and low surface area, typically below 10 m²/g, and pore diameter larger than 1000 Å. Typical examples of such materials are the siliceous skeletons of diatoms, i.e. diatomaceous earth such as Celite, (Manville Trademark). Other means of creating macroporosity consists of blending volatile or decomposable organic compounds which leave open space or pores after the material is calcined. Such materials are naphthalene, methylcellulose, polyvinylalcohols and urea.

(b) Making a mix of the spray-dried powder with water appropriate for the forming method to be used in step (c). We call this state "plasticized". If the diatomaceous earth was not added in step (a), it should be added here. Total diatomaceous earth from addition in either or both of steps (a) and/or (b) should be abut 10% to about 60% by weight based on the final calcined catalyst.

Typical water contents of the plasticized mix are between about 5% and 50% water.

(c) Forming the plasticized mix.

The preferred forming method is extrusion since the pellet diameter has to be as small as possible, i.e. in between 1/20" and 1/16". Extrusion of flutes is preferred for maximizing the surface of the pellets.

(d) Drying and calcining the formed material.

The porosity of the final catalyst is characterized by being bimodal, i.e. two ranges of pore diameters. One is between 1 and 0.1 micron, called the access pores, which allow better mass transfer of products and reactants. The second mode is represented by pores having diameters less than 500 Å, i.e. about 10 to about 200 Angstroms, and containing the catalytic centers.

The minimum desirable crush strength of our material at 1/16" is five pounds by the single pellet ASTM test D4179; for ⅛", it is eight pounds. These are both achieved by the above method.

EXAMPLE 1

An anionic clay was made by the method described in Example 1 of (parent) U.S. Pat. No. 4,970,191 without drying and calcining. That is, 81.6 g of glacial acetic acid was added to a slurry containing 89 g of pseudo-boehmite ("Versal 850") and 200 ml of deionized water, the mixture being continuously agitated. After 30 minutes approximately, 2 liters of deionized water and 57.6 g of magnesium oxide (Magchem 10-325 from Martin Marietta) were added and the resulting mixture was continuously agitated and heated to 85°-95° C. for 7 hours. This amount of magnesium oxide corresponds to a Mg/Al atomic ratio of 2.6. A sample of the aqueous suspension, as obtained after synthesis, was dried at room temperature on a glass slide and then analyzed by X-ray diffraction. The same sample was then dried at 110° C. and analyzed. The values of d-spacings, related to the interlamellar distance of the layered structure, are reported in the table below.

| d-spacing (Å) | drying temperature | |
|---|---|---|
| | 25° C. | 100° C. |
| d002 | 12.27 | 8.76 |
| d004 | 6.30 | 4.41 |
| d006 | 4.15 | n.a. |

Instead of drying as above, a sample of the aqueous suspension containing approximately 5 wt% solids was spray-dried at 90° C. The recovered powder, characterized by having particle sizes between 10 and 40 μm in diameter and by having a particle shape and structure as shown in FIG. 1, was used to make an extrusion mix by adding about 0.8 to 1.0 g of water per gram of spray-dried powder. A small sample of the mix was dried on a glass slide at 25° C. and analyzed by X-ray diffraction. The results are reported in the next table

| d-spacing | drying temperature 25° C. |
|---|---|
| d002 | 12.00 |
| d004 | 6.10 |
| d006 | n.a. |

The mix was extruded with a 1" extruder equipped with a 1/16" die. The wet extruded material was cut into pellets of about 3/16" in length, dried at 110° C. and calcined at 425° C. The final extrudates had a crush strength of about 20 lbs.

COMPARATIVE EXAMPLE 1

A sample of the aqueous suspension of Example 1 was dried in an oven at 110° C. The resulting solid was then milled into a fine powder which was used for making a mix with water and for making 1/16" extrudates as described in Example 1. The material recovered after drying and calcination had a crush strength of about 1.8 lb. Such material is too fragile and not suitable to be used in a commercial reactor.

EXAMPLE 2

An anionic clay suspension was made by the co-precipitation method as described in example 1 of U.S. Pat. No. 4,458,026 (not applicants, invention). The washed filter cake was diluted with water and the suspension was spray-dried at 90° C.; the resulting powder was used to make 1/16" extrudates. After drying and calcination, the final material had a crush strength of about 3.5 lbs.

COMPARATIVE EXAMPLE 2

The anionic clay suspension of Example 2 was dried in an oven at 110° C. and milled into a fine powder. By applying the same forming method as Example 2, the final material had a crush strength of about 1.5 lb.

EXAMPLE 3

An anionic clay aqueous suspension was made as in Example 1. About 25 wt% of Celite 545 (diatom material manufactured by Manville) was added to the suspension relative to its anionic synthetic clay content. The resulting mixture was spray-dried at 90° C. The spray-dried powder was then mixed with water to form a mix which was then extruded into 1/16" flutes. The flutes were dried in an oven at 110° C. and calcined at 425° C. in a muffle furnace for 4 hours. This material had a crush strength of about 10 lbs.

EXAMPLE 4

450 ml of the catalyst obtained in Example 3 was loaded into a 1" tubular reactor. Acetone vapor was passed through the reactor at an LHSV of about 2.0, a pressure of about 20 psig and a temperature of about 285° C. The reactor outlet was condensed and analyzed by gas chromatography. The results obtained at several different points of time on stream are reported in the table below.

| | 400 hours | 800 hours | 1200 hours |
|---|---|---|---|
| | Wt % of reactor effluents | | |
| acetone | 79.8 | 80.8 | 80.5 |
| mesityloxide | 3.2 | 3.3 | 3.6 |
| isophorone | 14.3 | 13.4 | 13.7 |
| high boiling products | 2.7 | 2.4 | 2.2 |
| | Selectivities (wt %) | | |
| mesityloxide | 15.7 | 17.3 | 18.4 |
| isophorone | 70.6 | 70.2 | 70.2 |
| heavies | 13.7 | 12.5 | 11.4 |
| | Selectivities (wt %) normalized at 20% conversion | | |
| mesityloxide + isophorone | 88.3 | 88.7 | 90.0 |

EXAMPLES 5-7

In order to demonstrate the effect of pore diffusion, several catalysts of different sizes were tested for the aldol condensation of acetone to mesityloxide and isophorone. The results obtained after 450 hours of reaction are shown in the table below.

| | Catalysts | | |
|---|---|---|---|
| | 1 | | 3 |
| | ¼" tablets | 2 | 40-70 Mesh |
| | Example 32 | 1/16" extrudates | made from |
| Reaction | U.S. Pat. No. | of Example 1 | extrudates |
| conditions | 4,476,324 | hereof | of col. 2 |
| LHSV | 0.9 | 2.0 | 2.0 |
| Temperature (°C.) | 300 | 290 | 290 |
| Pressure (Psig) | 40 | 15 | 10 |
| | Wt % of reactor effluents (dry basis) | | |
| acetone | 80.7 | 79.4 | 75.6 |
| mesityloxide | 3.7 | 2.3 | 1.9 |
| isophorone | 11.6 | 15.2 | 19.3 |
| high boiling products | 4.0 | 2.7 | 3.2 |
| conversion | 23.3 | 23.8 | 27.9 |

-continued

| | Catalysts | | |
|---|---|---|---|
| Reaction conditions | 1<br>¼" tablets<br>Example 32<br>U.S. Pat. No.<br>4,476,324 | 2<br>1/16" extrudates<br>of Example 1<br>hereof | 3<br>40-70 Mesh<br>made from<br>extrudates<br>of col. 2 |
| | Selectivities (wt %) | | |
| mesityloxide + isophorone | 79 | 85 | 87 |
| mesityloxide + isophorone normalized at 20% conversion | 81.9 | 87.4 | 90.7 |

EXAMPLES 8-10

An anionic clay suspension made by the method of Example 1 hereof was used to make three catalyst samples respectively containing 0, 15 and 30 wt% Celite 545. The Celite was added to the aqueous suspension prior to spray drying; the weight percent Celite given above is based on the calcined final catalyst. The catalysts, in the form of 1/20" extrudates, were tested for the condensation of acetone. The selectivities to mesityloxide and isophorone increased with the diatom content as reported in the next table below. The results are obtained after 200 hours of reaction.

| % Celite | wt % selectivities to mesityloxide and isophorone at 20% conversion of acetone | reduction of heavies compared to 0% Celite |
|---|---|---|
| 0% | 86.0 | — |
| 15% | 87.3 | 10% |
| 30% | 90.0 | 29% |

The samples were characterized by $N_2$ adsorption (BET surface area) and mercury penetration (Hg porosimetry). The results are shown in the table below. The samples containing Celite are bimodal.

| % Celite | porosity (cc/g) | pore diameter (Å) | BET Surface area ($m^2/g$) |
|---|---|---|---|
| 0 | 0.44 | 45 | 245 |
| 15 | 0.43 | 60 and 2000 | 228 |
| 30 | 0.38 | 60 and 3000 | 138 |

We claim:

1. Method of making a diffusion efficient, physically strong catalyst material from a synthetic clay having the general formula $$(Mg_{1-x}Al_x)(OH)_2 \cdot x\, A$$

where x is a number from 0.1 to 0.5, A is a univalent organic anion of the formula $RCOO^-$, R is $C_nH_{2n+1}$ and n is 0–4, comprising (a) spray-drying a slurry of said synthetic clay to produce particles having sizes between about 10 to about 100 microns in diameter and a residual water content of about 5 to about 50%, (b) making a plasticized mixture of said particles by adding water thereto, (c) forming said plasticized mixture into desired physical shapes and sizes, and (d) drying and calcining said physical shapes.

2. Method of claim 1 wherein about 10% to about 60% (based on the final calcined catalyst) diatomaceous earth is added to the slurry of step (a) prior to spray drying.

3. Method of claim 1 wherein about 10% to about 60% (based on the final calcined catalyst) diatomaceous earth is added to the plasticized slurry of step (b).

4. Method of claim 1 wherein the forming process of step (c) is an extrusion step.

5. Method of claim 4 wherein the extrusion process employs a multi-lobed die having a diameter no greater than about 3/16 inch.

6. Method of claim 1 wherein the forming process of step (c) is a pelletizing process and the pellets made thereby have an average diameter no greater than 3/16 inch.

7. Method of claim 1 wherein the particles obtained in step (a) have randomly-shaped open cells.

8. Catalyst made by the process of claim 2, having a bimodal porosity, including micropores of about 10 to about 200 Angstroms and macropores of about 1000 to 10,000 Angstroms.

9. Catalyst made by the process of claim 3, having a bimodal porosity, including micropores of about 10 to about 200 Angstroms and macropores of about 1000 to 10,000 Angstroms.

10. Catalyst made by the process of claim 4, having a bimodal porosity, including micropores of about 10 to about 200 Angstroms and macropores of about 1000 to 10,000 Angstroms.

* * * * *